United States Patent [19]

Veazey et al.

[11] Patent Number: 5,073,300

[45] Date of Patent: Dec. 17, 1991

[54] CORROSION INHIBITORS

[75] Inventors: Richard L. Veazey, E. Windsor, N.J.; Ewa A. Bardasz, Langhorne, Pa.

[73] Assignee: Union Camp Corporation, Wayne, N.J.

[21] Appl. No.: 503,185

[22] Filed: Apr. 2, 1990

Related U.S. Application Data

[62] Division of Ser. No. 206,451, Jun. 14, 1988, Pat. No. 4,946,629.

[51] Int. Cl.$^5$ .............................................. C23F 11/10
[52] U.S. Cl. .................................. 252/392; 564/169
[58] Field of Search .................. 525/275; 252/392; 527/275; 564/169

[56] References Cited

U.S. PATENT DOCUMENTS

| | | | |
|---|---|---|---|
| 3,873,501 | 3/1975 | Saga | 549/240 |
| 4,332,733 | 6/1982 | Samejima et al. | 549/240 |
| 4,694,059 | 9/1987 | Veazey | 525/275 |
| 4,997,907 | 3/1991 | Marlen et al. | 528/272 |

OTHER PUBLICATIONS

WO90/03405 "Tough, High Performance, Addition-Type Thermoplastic Polymers" Pater et al., Apr. 5, 1980.

*Primary Examiner*—Deborah L. Kyle
*Assistant Examiner*—Valerie D. Fee
*Attorney, Agent, or Firm*—Edward J. Sites

[57] ABSTRACT

The Diels-Alder adduct of 2,3 and 6,7 poly(allocimene) and an activated olefin such as maleic anhydride serves to inhibit the corrosion of metals. The adduct or a derived polyamine reaction product in admixture with an oil such as a petroleum oil or grease is effective to inhibit rusting of ferrous metals.

5 Claims, No Drawings

CORROSION INHIBITORS

This is a division of application Ser. No. 206,451 filed June 14, 1988 now U.S. Pat. No. 4,946,629.

BACKGROUND OF THE INVENTION

1. Field of the Invention

The invention relates to compositions and methods for inhibiting corrosion of metals and more particularly to a method employing oil-based corrosion inhibitor compositions.

2. Brief Description of the Prior Art

The prior art literature is replete with descriptions of a wide variety of methods and compositions for inhibiting the corrosion of metals, particularly ferrous metals. The massive bulk of literature on this subject over many years, is itself evidence of the lack of complete satisfaction with methods and compositions heretofore available to the artisan. The lack of full satisfaction is due to a broad variety of factors, such as cost, inefficiency of method, toxicity of compositions, relative ineffectiveness, incompatibility of compositions, and difficulty in handling.

One U.S. patent which is representative of the prior art descriptions is the U.S. Pat. No. 3,762,873 to Oude Alink (Oct. 2, 1973). This patent describes the use of substituted succinimides formed by reacting a hydrocarbon with a maleic compound and then reacting the product with an amine to form an imide. The imide structure is essential and imides are of course well recognized as corrosion inhibitors.

The inhibitors employed in the present invention are not imide compounds, but are effective corrosion inhibitors, particularly useful in an oil-based carrier composition such as a petroleum oil or grease.

SUMMARY OF THE INVENTION

The invention comprises a method of inhibiting corrosion of a metal exposed to oxidative conditions, which comprises; applying to said metal a corrosion inhibiting proportion of the Diels-Alder adduct of an activated olefin and a poly(alloocimene) having conjugated double bonds in pendant side chains.

The invention also comprises the Diels-Alder adduct of an activated olefin and a poly(alloocimene) having conjugated double bonds in pendant side chains, dispersed in an oil carrier composition.

The compositions and the method of the invention are useful to inhibit corrosion of metals particularly rusting of ferrous metals.

The term "activated olefin" as used herein means an olefin substituted with an electron-withdrawing group.

DETAILED DESCRIPTION OF THE PREFERRED EMBODIMENTS OF THE INVENTION

The corrosion inhibitor compounds employed in the method and compositions of the invention are adducts of alloocimene polymers which comprise the homopolymer of alloocimene having a weight average molecular weight of from about 500 to 100,000 and which contain repeating or recurring chain moieties of the formulae:

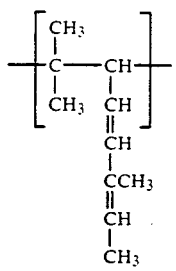

(I)

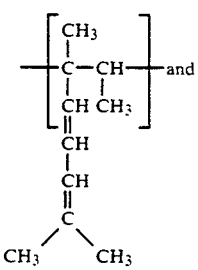

(II)

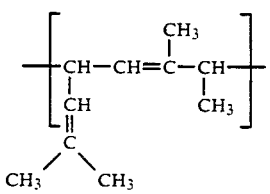

(III)

These poly(alloocimene) polymers comprise mixtures of polymer chains having a majority of chain moieties (I) and (II) and a minority of chain moiety (III). We define the mixture as 2,3 and 6,7 poly(alloocimene), i.e.: as that composition consisting of greater than 50 weight percent 2,3 poly(alloocimene), (I), and 6,7 poly(alloocimene), (II), and less than 50 weight percent of 4,7 poly(allocimene), (III).

The 2,3 and 6,7 poly(alloocimene) described above is a known polymer, which may be prepared by the method described in the European Patent Application Publication No. 0224829, European Patent Bulletin No. 1987/24 (June 10, 1987).

The corrosion-inhibiting adducts employed in the method and the compositions of the invention are prepared by the Diels-Alder reaction of the 2,3 and 6,7 poly(alloocimene) described above, with an activated olefin. The Diels-Alder reaction is well known; see for example Martin and Hill (*Chem. Revs.*, 1961, 61, 537); and Huigsen, The Chemistry of Alkenes, S. Patai, Editor, Chapter II, Part V, p. 878. In general, the reaction comprises the thermal or catalyzed addition of an activated olefin (the dienophile) to conjugated double bonds residing in 2,3 and 6,7 poly(allocimene)

More specifically, the Diels-Alder reaction may be carried out by first charging the poly(alloocimene) in relatively pure or crude forms to a suitable reaction vessel with the dienophile. The mixture is stirred and heated to effect Diels-Alder adduction of the dienophile to the polymer. Adductions in the absence of catalyst may be carried out at temperatures of from about 25° C. to about 200° C., preferably from about 100° C. to about 150° C. under ambient pressures. Catalysts for the Diels-Alder reaction are well known and may be employed in catalytic proportions, i.e.: a proportion of from about 0.001 to about 10 weight percent of the reaction mixture. Representative of catalysts which may be employed are aluminum and zinc compounds. In the presence of such catalysts the reaction temperature is normally from about 0° C. to about 100° C., preferably around room temperature and under ambient (atmospheric) pressure.

The dienophile is an activated olefin, that is, an olefin substituted with an electron-withdrawing group or groups. Examples of such groups are carbonyl, nitrile, nitro, sulfoxide, sulfone, sulfonyl and halogen. Representative of olefin dienophiles are maleic anhydride, acrylic acid, methacrylic acid, crotonic acid, itaconic acid, fumaric acid, quinone, aryl and alkyl acrylates such as isobornyl acrylate, methyl acrylate, methacrylate and like acrylate and methacrylate esters, polyol acrylates and polyol polyacrylates such as butanediol diacrylate, trimethylolpropane triacrylate, glycerol triacrylate, pentaerythritol tetraacrylate and the like, acrolein, acrylonitrile, vinyl sulfone, methyl vinyl ketone, nitroethylene, tetracyanoethylene, dichloroethylene, trichloroethylene, tetrachloroethylene, maleonitrile, monoesters and diesters of maleic acid, monoesters and diesters of fumaric acid, amides and bisamines of maleic acid, amides and bisamides of fumaric acid, acetylene-monocarboxylic acids, acetylenedicarboxylic acids, monesters and diesters of acetylenedicarboxylic acid, the like and maleiimides of the formula:

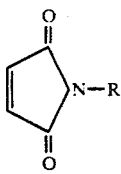

(IV)

wherein R is a monovalent group selected from alkyl and aryl. The term "alkyl" as used herein means the monovalent moiety obtained upon removal of a hydrogen atom from a parent hydrocarbon. Representative of alkyl are methyl, ethyl, propyl, butyl, pentyl, hexyl and isomeric forms thereof. The term "aryl" as used herein means phenyl, naphthyl and like groups.

The olefin dienophile may be added to the Diels-Alder reaction mixture in any amount; preferably an amount less than 100 mole percent of the amount of conjugated double bonds of the poly(alloocimene) to obtain a polymer with less than 75 percent of complete adduction, i.e.; to react with less than 75 percent of the conjugated bonds.

The Diels-Alder adduction is preferably carried out in the presence of an inert solvent. The term "inert solvent" is used herein to mean a solvent for the reactants which does not enter into or adversely affect the desired course of the reaction. Representative of inert solvents are toluene and xylene, which can dissolve both the polymer and the dienophile and which boil at the desired reaction temperature. In this case, the adduction is carried out simply by charging the solvent, polymer, and dienophile to the reaction vessel, and then heating to reflux temperature. Maintaining reflux temperature until adduction is complete, typically 1-30 hours depending on the solvent and dienophile chosen, results in the desired adduct polymer. The completion of the adduction may be observed by conventional and periodic analysis of the reaction mixture. For example infared analysis will show the appearance of spectra characteristic of the adduct polymers.

At the conclusion of the adduction reaction the desired product may be separated from the reaction mixture by conventional technique. For example, unreacted reagent and solvent may be separated by distillation.

The preferred adducts employed in the method and the composition of the invention are the maleic anhydride adducts, most preferably prepared by the adduction of from about 5 to less than 85 percent of the conjugated double bonds present in the poly(alloocimene); most preferably from about 20 to about 50 percent and advantageously from about 20 to 30 percent. Thus, the preferred adducts will comprise polymer chains containing repeating or recurring chain moieties of the formulae:

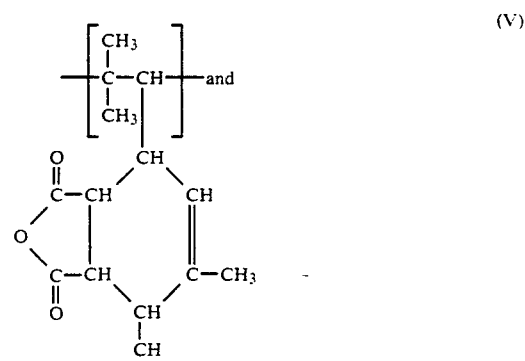

(V)

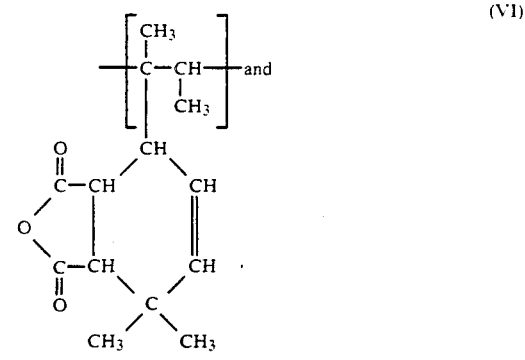

(VI)

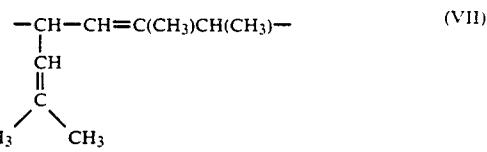

(VII)

wherein the chain units of the formula (V) and (VI) together constitute from 5 to less than 85 percent of the units of the formulae (I) and (II) found in the unadducted 2,3 and 6,7 poly(allocimene) described previously.

A preferred class of corrosion inhibitors of the invention are derivatives of the above-described adducts, prepared by the reaction of the adducts with a polyamine. Although we are not to be bound by any theory of operation, we believe that the adduct-polyamine reaction product is one wherein the oxirane ring opens and the amine reactant forms a substituent on the pendant side chains shown in the formulae (V), and (VI) given above. Amide groups are formed. This preferred adduct-polyamine reaction product apparently improves bonding in some way to metal surfaces. Corrosion inhibitors incorporated into petroleum products function by reaction chemically with metal surfaces to form thereon a corrosion-resistant, protective film or coating. This film must adhere tightly to the metal surface, lest it is removed by dispersants or detergents Exposure of a small area of the underlying metal surface can lead to catastrophic attack by acidic contaminants within lubricating oil.

The adduct-polyamine reaction product corrosion inhibitors of the invention may be prepared by the reaction of the adducts described above with a polyamine, at a temperature within the range of from about 50° C. to 200° C. for a period of time sufficient to obtain the desired substitution (generally from 2 to 8 hours, depending on the temperature selected). Advantageously, the reaction is conducted under an inert gas atmosphere, such as under a blanket of nitrogen or like inert gas. The presence of an inert organic solvent such as mixed xylenes will also promote the desired reaction.

The polyamine reactants employed in preparing the adduct-polyamine product are well-known compounds, as are the methods for their preparation. Representative of such polyamines are those of the formula:

$$H_2N \text{\textendash} (R\text{\textemdash}NH)_n\text{\textendash}H \qquad (VIII)$$

wherein R represents hydrocarbylene and n is an integer of from 2 to 5.

The term "hydrocarbylene" as used herein means the divalent moiety obtained by removal of a hydrogen atom from each of two carbon atoms in a parent hydrocarbon. Representative of hydrocarbylene are alkylene such as ethylene, propylene, butylene, pentylene, hexylene, heptylene, octylene and isomeric forms thereof; arylene such as phenylene, naphthalene and the Representative of the polyamines of the formula (VIII) are ethylene diamine, hexamethylene diamine, diethylene triamine (DETA), diethyleneaminopropylamine, m-phenylene-diamine, p-phenylenediamine, methylenedianiline, triethylene tetraamine (TETA), tetraethylene pentamine and the like.

The proportion of polyamine (VIII) employed to prepare the adduct-polyamine reaction product may vary widely but is preferably from 0.25 to 1.5 moles per polymer chain units of the formula (V) and VI) calculated to be present in the poly(alloocimene) adduct reactant. In preferred adduct-polyamine reaction products, from 25 to 100 percent of the polymer chain units of the formulae (V) and (VI) will be reacted with the polyamine reactant of the formula (VIII).

The corrosion inhibiting compositions of the invention are prepared by the simple admixture of a metal corrosion inhibiting proportion of the above-described adducts and/or their polyamine derivatives with an oil carrier such as a petroleum oil or grease. Preferred a the oil carrier is a mineral oil. A corrosion inhibiting proportion is defined herein as that proportion which will inhibit oxidation of the metal in the presence of an oxidant such as oxygen. In general, a corrosion inhibiting proportion will comprise from about 0.1 to 5.0 percent by weight of the composition. The precise proportion required is dependent upon the percentage of adduction found in the particular adduct or polyamine derivative employed. In general, the lower the percentage of adduction, the greater will be the required proportion of adduct in the oil carrier.

The following examples describe the manner and the process of making and using the invention and set forth the best mode contemplated by the inventor for carrying out the invention, but are not to be construed as limiting.

PREPARATION 1

To a clean, oven-dried, four neck round-bottomed flask, equipped with a thermometer, nitrogen inlet, pressure equalizing addition funnel, a reflux condenser into which was inserted an inert gas exit adapter, and a Nicrome wire stirrer, was added sodium shot (46 g) and toluene (300 ml) which had been dried and distilled from calcium hydride A nitrogen blanket was maintained in the reaction flask at all times. Heat was applied and stirring initiated. The toluene was allowed to gently reflux for 30 minutes, and then it was cooled. At this point tetrahydrofuran (250 ml) was added. A pre-weighed sample of alloocimene (1242 g, 44.5% true) which had been dried over calcium hydride and distilled, was charged to the addition funnel. The polymerization temperature of 60° C. was maintained by applying heat with a heating mantle attached to a temperature sensing device. Polymerization was initiated by slowly adding the alloocimene mixture over a period of one hour to the stirred solvent containing sodium metal. After 4.5 hours, the polymerization was complete and the poly(alloocimene) was isolated by transferring the polymer solution into a separatory funnel containing methanol. After deactivation of the catalyst, water and toluene were added, and the polymer solution was thoroughly washed with water. The organic solution was then dried over anhydrous magnesium sulfate and filtered into a round-bottom flask. The solvent was removed at reduced pressures. Any monoterpenes were isolated at approximately 65° C. (5 to 20 mm Hg.). The distillation was terminated when the temperature in the pot containing the polymer product reached about 150° C. The polymer was poured while hot into a pan, allowed to cool, then stored under nitrogen. The polymer had a weight average molecular weight of 800.

PREPARATION 2

Poly(alloocimene) prepared by the procedure of Preparation 1, supra., (10 g, 0.074 moles of terpene units) and maleic anhydride (7.25 g, 0.074 moles) was charged to a reaction flask and heated at 140° C. for 3 hours. A small amount of unreacted maleic anhydride was removed by distillation under vacuum. The adduct resin had a saponification number of 240 (theory for complete adduction of all terpene units is 481, indicating about 50% adduction).

PREPARATIONS 3-6

The procedure of Preparation 2, supra., was repeated a plurality of times, varying the proportions of maleic anhydride to obtain adducts with 5, 10, 20 and 30 percent adduction, respectively.

EXAMPLE 1

The adduct preparations of Preparations 2-6, were admixed in various proportions with a light mineral oil (Rudol) having a viscosity within the range of 145-155 SSU at 37.8° C. The oil based compositions were then tested according to the method of ASTM test procedure D-665-A. In this test, a mixture of 300 ml of the oil under test is stirred with 30 ml of distilled water at a temperature of 60.0° C. with a cylindrical steel specimen completely immersed within After 24 hours immersion, the appearance of the metal surface is rated. In order to report an oil as passing or failing, the test must be conducted in duplicate. An oil is reported as passing the test (P) if both specimens are rust-free at the end of the test period. An oil is reported as failing (F) the test if both specimens are rusted at the end of the test period. If one specimen is rusted while the other is free of rust, tests on two additional specimens are made.

The test results obtained in this example are shown in the following TABLE 1 together with comparisons to test results observed for the mineral oil base carrier alone as a control and for the unadducted polymer of Preparation 1, supra. The proportions of adduct employed are also shown in the TABLE 1, below.

TABLE 1

| ADDITIVE CONCENTRATION (WGT %) | OIL (CONTROL) | ADDUCT (% ADDUCTION) | | | | | |
|---|---|---|---|---|---|---|---|
| | | 0 | 5 | 10 | 20 | 30 | 50 |
| 0.0 | F | — | — | — | — | — | — |
| 0.1 | — | F | F | F | P | P | — |
| 0.25 | — | F | F | F | P | P | F |
| 0.5 | — | F | P | P | P | P | P |

The blend of adduct prepared with 20 percent adduction was also tested to determine its oxidation stability, by ASTM test method D-943. The method is used to estimate the oxidation stability of lubricants, in the presence of oxygen, water and copper/iron metals at elevated temperatures. The procedure is as follows:

The oil sample (300 ml) is purged with oxygen in the presence of water (60 ml) and an iron-copper coil at 95° C. A blend is reported as passing the test if its total acid number does not exceed value of 2.00 mg KOH/g during first 500 hours. Test continues until the critical acid number is reached. The number of test hours required for the oil to reach 2.0 mg KOH/g is defined as the "oxidation lifetime" and it is reported in hours.

The test result was a finding or more than 500 hours (passed).

EXAMPLE 2

A quantity (782.4 g) of poly(alloocimene)-maleic anhydride adduct (20% adduction) prepared in accordance with the procedure of Preparation 5, supra, was charged to a suitable reaction vessel fitted with a condenser. The air in the vessel was purged with nitrogen gas. The charge was heated to a temperature of 90° C. and 916.15 g of mixed xylenes was added as solvent. With stirring, there was added dropwise to the reaction solution, 130.1 g, 1.26 moles of diethylene triamine (DETA). The addition took 60 minutes. The reaction solution was heated up to 98° C. by the addition of the DETA. Some light orange solid formed within the reaction solution during the addition The reaction solution was then heated up to a temperature of 130° C. over a 4.5 hour period of time. About 16 ml of water collected in the trap. The reaction solution was then cooled to a temperature of 50° C. and vacuum distilled to remove solvent. The adduct-polyamine product is a light orange, viscous liquid with a glass transition temperature as measured by differential scanning calorimetry of acid, and amide carbonyl groups.

EXAMPLE 3

A clean, dry 250 ml 4-neck round bottom-flask was equipped with a paddle blade stirrer, a reflux condenser, a Claisen adaptor, a nitrogen inlet and thermometer, and a rubber septum. The space within the equipment was purged 5 minutes with dry nitrogen. The inside of the flask was then blanketed with nitrogen. To this flask was added 30.4 g of Preparation 5 supra., (20 percent maleic anhydride adducted polyalloocimene), 60 ml of mixed xylenes, and 6.03 g of triethylene tetraamine (TETA). Stirring was initiated.

The reaction was started by heating the solution to 130° C. over a 2.5 hour period. The reaction temperature was held at 130° C. for 7 hours. The reaction mixture was then cooled to 60° C., and the equipment set up for Vaccuum distillation. Vacuum was applied and the reaction mixture was slowly heated to 140° C. over a 2 hour period. An orange liquid was obtained. The infrared spectrum of this product showed the presence of anhydride, acid and amide groups.

EXAMPLE 4

The adduct-polyamine products obtained in each of the Examples 2 and 3, supra., were separately admixed in various proportions with Rudol, supra., and the resulting mixtures tested as described in Example 1 supra. The test results are shown in the TABLE 2. below.

TABLE 2

ANTIRUST PERFORMANCE OF DETA/ TETA SUBSTITUTED POLY(ALLOOCIMENE)- MALEIC ANHYDRIDE ADDUCTS

| Additive concentration | Additive of Example 2 | Additive of Example 3 |
|---|---|---|
| 0.0 (wgt %) | Failed | Failed |
| +0.01 | Failed | NT* |
| +0.025 | Passed | NT* |
| +0.05 | Passed | Failed |
| +0.1 | Passed | Passed |
| +0.25 | Passed | Passed |
| +0.5 | Passed | Passed |

*NT = Not Tested

Aliquots of the compositions prepared according to the procedure of EXAMPLE 1, supra., and Example 4 (using the compound of Example 2), both containing 0.25 percent by weight of the corrosion inhibitor of the invention, were also subjected to the following performance tests.

1. THERMAL STABILITY, CORROSIVITY BEHAVIOR OF LUBRICANT BLENDS MIL-L-236999c)

This test is widely used to estimate thermal stability and corrosive tendencies of lubricant blends exposed to elevated temperatures while contacted by ferric specimen.

Procedure

Blend sample (100 ml) contacts iron coupon at 273.8° C. for 96 hours. Prior to the test and upon the completion of the test, the blends' viscosity and total acid number is measured. Corrosion rates, based on the coupon's weight loss, and changes in metal surface appearance are also reported.

A blend is reported as passing the test when its viscosity change does not exceed 5%, and the total acid number change does not exceed 6.0, and the specimen weight change does not exceed 4 mg/cm$^2$. The test results are shown below in TABLE 3.

TABLE 3

RESULTS OF THERMAL STABILITY, CORROSIVITY TESTS

| | EXAMPLE 1 | EXAMPLE 4 |
|---|---|---|
| Viscosity Change, % | +0.08 | +0.04 |
| TAN Change | +0.09 | +0.09 |
| Specimen Wt. Change. mg/cm$^2$ | 0.0 | 0.0 |

TABLE 3-continued
RESULTS OF THERMAL STABILITY, CORROSIVITY TESTS

|  | EXAMPLE 1 | EXAMPLE 4 |
|---|---|---|
| Corrosion - Above Liquid | None | None |
| - Below Liquid | None | None |
| Overall Test Results | Passed | Passed |

2. FOAMING CHARACTERISTICS OF LUBRICANT BLENDS: ASTM TEST METHOD D-892

The test defines the foaming characteristics of blends at two temperatures: 23.9° C. and 93.3° C. It is used in the selection of lubricants suitable for high speed gearing, high volume pumping, or splash lubrication.

Procedure

A constant volume of oil (200 ml) is purged with air (95 ml/min) according to a sequential pattern described below:

Sequence I: 5 minutes aeration at 23.9° C. (foam volume reported) is followed by 10 minutes setting time (foam volume reported).

Sequence II: 5 minutes aeration at 93.3° C. (foam volume reported) is followed by 10 minutes setting time (foam volume reported).

Sequence III: 5 minutes aeration at 23.9° C. directly following Sequence II is followed by 10 minutes setting time.

In order to pass the test, the reported foam volume following the setting period should be reduced to zero. The test results are shown below in TABLE 4.

TABLE 4
FOAM CHARACTERISTICS TEST RESULTS

|  | EXAMPLE 1 | EXAMPLE 4 |
|---|---|---|
| Sequence I, 23.9° C. | | |
| Volume, 5 min. aeration, ml | 170 | 100 |
| Volume, 10 min. setting, ml | 0 | 0 |
| Sequence II, 93.3° C. | | |
| Volume, 5 min. aeration, ml | 20 | 30 |
| Volume, 10 min. setting, ml | 0 | 0 |
| Sequence III, 23.9° C. | | |
| Volume, 5 min. aeration, ml | 90 | 100 |
| Volume, 10 min. setting, ml | 0 | 0 |
| Overall Test Results | Passed | Passed |

What is claimed is:

1. The reaction product of (A) the Diels-Alder adduct of 2,3 and 6,7 poly(alloocimene) and an activated olefin and (B) a polyamine.

2. The product of claim 1, wherein the activated olefin is maleic anhydride.

3. The product of claim 1 wherein the polyamine is selected from those of the formula:

wherein R represents hydrocarbylene and n is an integer of from 2 to 5.

4. The product of claim 3 wherein the polyamine is diethylene triamine.

5. The product of claim 3 wherein the polyamine is triethylene tetraamine.

* * * * *